United States Patent [19]

Koebler et al.

[11] Patent Number: 5,023,187
[45] Date of Patent: Jun. 11, 1991

[54] METHOD AND DEVICE FOR ACCELERATED TREATMENT OF THIN SAMPLE ON SURFACE

[75] Inventors: Douglas J. Koebler, Irwin; Carlo Cuomo, Verona, both of Pa.; David J. Brigati, Edmond, Okla.

[73] Assignee: Fisher Scientific Company, Pittsburgh, Pa.

[21] Appl. No.: 168,173

[22] Filed: Mar. 15, 1988

Related U.S. Application Data

[63] Continuation-in-part of Ser. No. 775,864, Sep. 13, 1985, Pat. No. 4,731,335, and a continuation-in-part of Ser. No. 32,874, Mar. 31, 1987, Pat. No. 4,801,431.

[51] Int. Cl.$^5$ .................. G01N 1/10; G01N 1/30; B01L 7/00; B01L 9/00
[52] U.S. Cl. .................. 436/180; 73/863.11; 73/864.72; 118/641; 211/41; 219/354; 219/411; 250/432 R; 250/492.1; 422/100; 422/104; 424/3; 427/2; 427/4; 427/55; 436/63; 436/174
[58] Field of Search .................. 436/34, 180, 501, 63, 436/162, 174; 118/641; 427/2, 4, 55; 211/41; 422/99, 100, 102, 104; 73/864.72, 863.11, 864.02; 350/534, 536; 250/429, 432 R, 492.1; 219/10.65, 354, 411; 156/380.9; 424/3

[56] References Cited

U.S. PATENT DOCUMENTS

| | | | |
|---|---|---|---|
| 2,119,407 | 5/1938 | Weiskopf | 211/41 |
| 2,282,070 | 5/1942 | Manahan | 34/150 |
| 2,515,731 | 7/1950 | Page | 219/411 |
| 2,668,364 | 2/1954 | Colton | 219/354 |
| 2,863,319 | 12/1958 | McLin | 422/100 |
| 3,306,835 | 2/1967 | Magnus | 250/492.1 |
| 3,358,496 | 12/1967 | Farmer | 73/864.72 |
| 3,837,795 | 9/1974 | Becker et al. | 427/4 |
| 4,043,292 | 8/1977 | Rogers et al. | 118/5 |
| 4,199,613 | 4/1980 | Johnson | 427/4 |
| 4,377,641 | 3/1983 | Dee et al. | 436/162 |
| 4,567,847 | 2/1986 | Linner | 118/50.1 |
| 4,731,335 | 3/1988 | Brigati | 118/421 |
| 4,751,372 | 6/1988 | Fraas | 219/354 |
| 4,818,680 | 4/1989 | Collins et al. | 436/501 |
| 4,853,327 | 8/1989 | Dattagupta | 435/810 |

FOREIGN PATENT DOCUMENTS

| | | |
|---|---|---|
| 8700004 | 1/1987 | PCT Int'l Appl. |
| 251168 | 7/1948 | Switzerland |
| 2152700 | 8/1985 | United Kingdom |
| 2180647 | 4/1987 | United Kingdom |

OTHER PUBLICATIONS

P. J. Coates et al., "Rapid Technique of DNA-DNA in situ Hybridization . . . ", J. Clin. Pathol., vol. 40, pp. 864-869 (1987).
D. J. Brigati et al., "Detection of Viral Genomes . . . ", Virology vol. 126, pp. 32-50 (1983).
E. R. Unger et al., "Viral Diagnosis by in situ Hybridization", Am. J. Surg. Pathol., vol. 10, pp. 1-8 (1986).
D. J. Brigati et al., "Immunocytochemistry and Capillary Gap Technology", Jun. 1, 1987.
D. J. Brigati, "Advanced Immunoperoxidase Techniques Using Automated Immunocytochemistry" (workshop Mar. 7, 1987).
"Fisher Histomatic Code-On Series Slide Stainer" (Bulletin No. 885 printed 5/87).
Nathan T. Brinn, "Rapid Metallic Histological Staining Using the Microwave Oven", J. of Histotechnology, vol. 6, No. 3, pp. 125-129 (Sep. 1983).
Therma-Tech Corporation, "Therma-Tech Infrared Heaters and Systems" (Bulletin TT-0057-1-84; copyright 1983).

*Primary Examiner*—Michael Wityshyn
*Attorney, Agent, or Firm*—Alan M. Doernberg

[57] ABSTRACT

A thin sample on a surface such as a tissue specimen on a microscope slide is exposed to treatment liquid such as a stain, antibody of nucleic acid probe. The treatment is accelerated by exposing the treatment liquid on the surface to infrared radiation. A device is disclosed for placing such slides into a treatment chamber, for example as a plurality of slide pairs held vertically, with treatment liquid held in capillary gaps between each slide pair. An infrared radiation source provides radiation into the treatment chamber to accelerate the treatment of samples on such slide (on one or both surfaces facing each capillary gap) by the treatment liquid.

24 Claims, 5 Drawing Sheets

METHOD AND DEVICE FOR ACCELERATED TREATMENT OF THIN SAMPLE ON SURFACE

This is a continuation-in-part of U.S. Ser. No. 775,864, filed Sept. 13, 1985 of Brigati now U.S. Pat. No. 4,731,335, issued March 15, 1988, and U.S. Ser. No. 032,874, filed March 31, 1987 of Brigati and Cuomo, (now U.S. Pat. No. 4,801,431) each commonly assigned and copending.

The present invention relates to the treatment of a thin sample on a surface in contact with a treating liquid, and especially to the acceleration of the treatment of thin samples such as tissue specimens by treating liquids such as histological and hematological stains, immunological reagents and nucleic acid probe reagents.

One type of instrument commonly used to treat thin samples with a treating liquid is an automated slide stainer. This instrument immerses slides bearing samples in a succession of treating liquids.

One such slide stainer marketed by Fisher Scientific Company from 1980 to 1986 was the HISTOMATIC Slide Stainer, Model 172 (Fisher 86 Catalog Number 15-185-172) which had a drying chamber into which a rack holding spaced, parallel, vertically-disposed slides could be automatically placed at the outset of the staining process. The instrument, if so programmed, would blow air over an electrically heated metal wire and convey the warm air into the drying chamber through the array of slides in order to melt the paraffin surrounding the formalin fixed tissues to increase their retention on the slides. Such wire was not designed to become red hot, nor was its placement in the instrument suitable for radiant heating of the slides.

Published PCT application WO 87/00004 of Bone Diagnostic Center Inc. (Jan. 15, 1987) describes a variety of applications for microwave radiation in the fixation, dehydration, embedding, mounting and staining of tissue, including, at pages 18-19, the use of microwave radiation to accelerate the staining of tissue samples on slides. Other uses of microwave radiation are described in various references reported in the search report published with WO 87/00004.

U.S. Pat. No. 4,567,847 of Linner (1986) describes apparatus and methods for cryopreparation of biological tissues for ultrastructural analysis. Col. 15 refers to various radiant heating means to controllably raise the temperature of the tissue. Various types of electromagnetic energy sources including microwaves are indicated as being suitable, alone or in combination with magnetic flux, except that infrared radiation should be avoided.

N. Brinn, "Rapid Metallic Histological Staining Using the Microwave Oven" J. of Histotechnology, vol. 6, no. 3, pp. 125–129 (1983) describes the acceleration of certain staining procedures by the use of microwave radiation. Slides were placed in plastic Coplin jars containing a stain solution (e.g., methenamine silver working solution), a cap loosely screwed onto the jar and the jar placed in a microwave oven for approximately one minute. In many cases, the slides were indicated as remaining in the hot working solution for seconds or minutes after the jars were removed from the oven. While the procedure is indicated as applicable to accelerate metallic and certain other staining procedures, the disclosure provides no alternative to the slide being immersed in a bath of the treating liquid at the time of exposure to microwave radiation. This immersion technique is applied to disperse the microwave energy, thereby helping to limit overheating of the tissue sections and their subsequent destruction.

U.S. Application No. 775,864 of Brigati, filed Sept. 13, 1985 (see also GB-A-2,180,647A, published April 1, 1987) describes methods for treating thin samples such as tissue on surfaces such as microscope slides involving capillary action. Briefly, treating liquid is drawn between two slides into contact with the sample on one (or both) slides by capillary action, especially being drawn vertically upward. In disclosed devices with multiple slide pairs held in parallel vertical arrays, the entire device is conveyed between reagent stations in an automatic slide stainer: alternately picking up treating liquids by contacting the base of each slide pair with liquid (in droplets or in pools), and then removing the liquid by contacting the base of each slide pair to an absorbent material. The slide holder shown in that application has a flange 451 extending outward so that the array with gaps filled with liquid can be placed in a 37 degree wet chamber located at one of the positions of the automated slide stainer. In the illustrative multi-step immunocytochemistry procedure, the slide array is placed in the wet chamber during step 13 filled with enzyme digestion reagent, during step 15 filled with blocking reagent, during step 17 filled with reagent containing biotinylated primary antibody, during step 20 filled with enzyme-containing reagent, and during steps 24 and 25 filled with chromagen reagent. UK Published Application GB 2,180,647A (April 1, 1987) contains the same disclosure.

An improved version of the slide holder and array is described in parent patent application U.S. Ser. No. 032,874 of Brigati and Cuomo, filed March 31, 1987 as a continuation-in-part of 775,864. The flange 51 shown in FIG. 2B of 032,874 (U.S. Pat. No. 4,801,431) would similarly act to complete the enclosure of the wet chamber when the slide array is placed in that station.

While the methods and devices of U.S. Application Nos. 775,864 and 032,874 offer enhanced control and savings in cost and time in multi-step treating processes, the time required for certain critical individual steps remains large. Thus, in the exemplary immunocytochemistry procedure of U.S. Application No. 775,864, the six periods in the wet chamber constitute 94 minutes out of an overall process time of 131 minutes when the time for robotic movements between stations is added to the basic reagent application times. While a modification of the procedure and careful control of individual steps may reduce these periods somewhat, there remains a minimum time period that the slide array must stand in the wet chamber for the indicated step to be completed (e.g., immunochemical binding or enzymatic color development). Furthermore, because of the use of metal in the slide holder, microwave radiation would be unsuitable for accelerating those steps.

BRIEF DESCRIPTION OF THE INVENTION

The present invention employs infrared radiation to accelerate the treatment of a thin sample by a treating fluid, especially when the treating fluid has been drawn into contact with the sample by capillary action. Accordingly, the present invention provides, in one form, a method for treating a thin sample on a surface which comprises:

(a) providing a thin sample on a first surface, (b) maintaining a second surface substantially parallel to and spaced by a first distance from the first surface, thereby providing a gap between the first and second surfaces, (c) introducing a treating liquid into the gap, (d) drawing the treating liquid by capillary action within the gap into contact with the thin sample, and (e) generating infrared radiation so as to expose the treating liquid in contact with the thin sample to the infrared radiation for a sufficient exposure level and time to accelerate the treatment of the thin sample by the treating liquid.

The present invention also provides a method for accelerating the treatment of a biological specimen by a treating liquid which comprises the steps:

(a) providing a thin sample on a first surface, (b) forming a thin layer of a treating liquid on the first surface in contact with the thin sample, (c) generating infrared radiation, and (d) exposing the thin layer of treating liquid to the infrared radiation at a sufficient exposure level and for a sufficient exposure time to accelerate the treatment of the thin sample by the treating liquid.

The present invention also provides a device for accelerated treatment of thin samples by treating liquid which comprises;

(a) a treatment chamber having a bottom wall and upstanding side walls, the treatment chamber forming an upper opening, (b) holding means for engaging the upper ends of a plurality of planar pieces and maintaining the planar pieces in parallel array extending downward from the holding means in a substantially vertical direction, (c) flange means associated with the holding means for cooperating with the holding means to substantially cover the upper opening formed by the treatment chamber, and (d) radiation means for generating infrared radiation within the treatment chamber with the flange means and holding means substantially covering the upper opening and for exposing the planar pieces to the infrared radiation.

DETAILED DESCRIPTION OF THE INVENTION

The method of the present invention includes contacting a thin sample on a first surface with a thin layer of a treating fluid, and then exposing the thin layer of treating fluid to infrared radiation to accelerate the treatment of the thin sample. In many forms of the invention, the thin layer of treating fluid is maintained in a gap between the first surface and a second surface, such as is described in U.S. Ser. No. 775,864 of Brigati. In certain of such forms a plurality of pairs of slides define a plurality of such gaps, and the portions of the gaps bearing the thin samples are within a treating chamber where the infrared radiation is provided. In the following description, such forms of the present invention involving a plurality of pairs of slides and a treatment chamber will be described first. Thereafter, representative other arrangements for practicing the present invention will be briefly described. It should be understood, however, that each feature described in first description may apply, but is not necessarily mandatory, to other arrangements for practicing the present invention.

In preferred forms of the present invention, a holder, or holding means, is provided to engage the upper ends of a plurality of planar pieces such as microscope slides. One especially preferred form of such holder is the type of slide holder described in U.S. Ser. No. 032,874 of Brigati and Cuomo, filed March 31, 1987 and commonly-assigned. In a first version of such slide holder (illustrated in FIG. 1 of U.S. Ser. No. 032,874 and in FIG. 5 of U.S. Ser. No. 775,864) slots are provided in the underside of the holder. Pairs of flat microscope slides are inserted into the slots with a shim such as a cover slip between the top ends of the two slides in each slot, so that the major portion of each slide pair extends below the holder and forms a gap between the two slides which is the thickness of the shim, e.g., 50–500 micrometers (um), preferably 100 to 250 um, especially 150 to 200 um.

A second form of slide holder is illustrated in FIGS. 2A–2D of U.S. Ser. No. 032,874 and FIGS. 1, 2 and 3 hereof. This slide holder has divider brackets extending downward from the horizontal cover of the holder, and pairs of vertically spaced clips on each divider bracket arranged so that slide pairs can be received within two clips on one side of the top portion of the slide pair and within two clips on a facing divider bracket on the other side of the top portion of the slide pair. Slides used for such slide pairs could be flat slides separated by a shim, but are preferably slides with coated upper surfaces which, when opposed, define the thickness of the gap below the coating portions. Such slides are described in more detail in U.S. Ser. No. 033,073 of Brigati filed, March 31, 1987 and commonly-assigned, now U.S. Pat. No. 4,777,020. It will be appreciated, however, that such coated slides could also be used to fit slide pairs into the slots of the holder of FIG. 5 of U.S. Ser. No. 775,864, provided that suitable elastomeric elements or the like are provided either on the back of one or both slides of a pair or on the interior of the slot to deform and exert a force on the slides that maintains the slide pair in the slot.

While such a holder could be used in the present invention to maintain a single slide pair, it is most advantageous that the holder have spaces for a large number of slide pairs, such as 10 to 100 pairs, more typically 20 to 60 slide pairs (30 slide pairs in the illustrative embodiments). It is not necessary, however, that the holder be completely full; and it is anticipated, particularly in applications such as histochemistry, immunocytochemistry and nucleic acid hybridization, that laboratories will run concurrently as many slide pairs as represent the specimens to be treated and evaluated at one time, as long as the treatment protocol permits concurrent processing. In this regard, however, it is not necessary that the samples in the gap of each slide pair be subjected to identical treatments since, as explained more fully in U.S. Ser. No. 775,864, the treating fluids supplied to each slide pair can be individualized by the use of reagent isolators. Thus, for example, in a multistep immunocytochemistry process, thirty slide pairs can be treated by methods that vary from identical treatment to thirty different treatment regimes, differing for example by having thirty different primary antibodies delivered one each to the thirty different gaps at one step of the process. What will generally be identical, however, is the series of time and temperature conditions to which each set of sample is subjected. Even then, however, if a particular treatment step (e.g., a digestion step) is desired to be omitted for some slide pairs, but not for others, it may be acceptable to draw inert buffer into the first group of slide pairs while digestion enzyme solution is drawn into the others, and then subject both to radiation in accordance with the present invention.

The geometrical arrangement of the surfaces (defined in the preferred cases by the slides of the slide pairs) is not critical to the present invention; but the preferred arrangement is for the slide pairs to extend vertically downward from the holder. It is often convenient for the slide pairs to be arranged in parallel rows, with the slide pairs in each row being parallel and spaced horizontally by a regular distance (described in various earlier applications as a second distance, typically 5-7 mm, whose significance pertains primarily to drawing individual aliquots of treating liquid into the gaps). The overall horizontal profile of the slide pairs is important in the present invention when a treatment chamber is to be provided which has an opening in its top wall of horizontal dimensions sufficiently large for the slide pairs to move freely through the opening.

Similarly, depending upon how infrared radiation is supplied in or into the treatment chamber, the slide pairs can be arranged to provide an even distribution of exposure of the radiation to each treating fluid in each gap. This limitation will be more significant when the radiation is directed horizontally (as in present FIG. 5) than when it is directed vertically upward (as in present FIG. 2). This limitation can be overcome by combining vertically and horizontally directed radiation in one treatment chamber. One way of so combining would be to polish or treat with a shiny silvered metallic surface the underside of the slide holder and the side walls of the treatment chamber, with the radiation source located at the base of the treatment chamber, so as to distribute and equalize the radiation among the gaps containing treatment fluid.

A preferred manner of providing infrared radiation to the treating fluid in contact with samples in the method of the present invention is through the use of a treatment chamber. Once the fluid and samples are in the treatment chamber, it is preferred that the chamber be closed to the extent that infrared radiation supplied to the interior of the chamber does not leak appreciably from the chamber as light. A preferred means for accomplishing such closure is to provide a treatment chamber with internally reflective bottom wall and upstanding side walls. Typically four side walls are employed, although rectangular horizontal cross-sections are not mandatory. In addition, such treatment chamber has a top surface that is partially or totally open in the absence of the holder. In such cases, the holder can seal off the top surface, preferably by having the holder extend horizontally in at least one direction beyond the horizontal profile of the slide pairs, e.g., in one or more flanges that engage or rest on either portions of a top wall of the treatment chamber or top edges of a side wall or side walls of the treatment chamber. The underside of the slide holder can be provided with a surface of a polished metal or other reflective surface. It is contemplated that a single treatment chamber with a top opening of a single size could be used in conjunction with multiple holders, each capable of holding slide arrays of different horizontal profiles, provided that each such horizontal profile of slide array can be received through the opening and that each holder has flanges or similar structure to cover the remainder of the opening not within the profile of the slide array.

Infrared radiation can be generated within the treatment chamber or, as discussed below, generated outside the treatment chamber and conveyed into the treatment chamber. For generation within the treatment chamber, the radiation source can be located at any location within the chamber that would no be occupied by slides, but is preferably located on the interior of a wall such as the bottom wall or one or more of the side walls. When a radiation source is located on the bottom wall, it is desirable to ensure against deleterious effects of treatment liquid depositing on the radiation source. Such depositing is unlikely to occur if all liquid brought into the chamber is in capillary gaps. The radiation device generally includes a heated element that emits infrared radiation and a cover element (usually ceramic) that protects the heated element and permits the transmission of infrared radiation.

By infrared radiation is meant electromagnetic radiation (light) of wavelength longer than visible light (longer than 750 nm or 0.75 um) up to 12,000 nm (12 um). By contrast, microwave radiation (employed in certain prior art methods described above) is generally understood to be of wavelength 1 to 300 mm (1000 to 30,000 um). The radiation between infrared and microwave in wavelength (i.e., 12 to 1000 um) is regarded as heat rather than light in terms of passage through air because the gas molecules in air absorb so much of this radiation that it is not an effective means for radiant heating.

The infrared radiation employed can peak in the near infrared (preferably 0.7 to 2.8 um) or in the far infrared (preferably 2.8 to 8 um), with the usual shape of energy versus wavelength having a reasonably sharp rise from lower wavelengths toward the peak region and a reasonably gradual decline from the peak region toward higher wavelengths. Infrared radiation of narrow bandwidth (e.g., from a laser) can also be employed. The THERMA-TECH Type B infrared panel used in the Examples is designed to emit from a source heated to up to 1200 degrees F. (650 C.) and to emit light through a ceramic cover primarily in the 3.5 to 6.0 um portion of the far infrared. Such panels are described by the manufacturer as being an efficient medium intensity heater, good where line speed is medium to high and only heat penetration of surface is needed. It is a general characteristic of infrared radiation, especially when compared to microwave radiation, that infrared radiation supplies energy to surfaces rather than penetrating.

The intensity of the radiation source can be controlled in a variety of ways, typically by monitoring one or more parameters and then adjusting the energy supplied to the source based on the results of such monitoring and the desired treatment conditions. For example, one could monitor the radiation itself with a photodetector; but it is preferred to sense temperature either of the cover on the light source or of some point within the treatment chamber (which may or may not be within the profile of array of slide pairs). For example, the illustrative Type B device is fitted, in some cases, by the manufacturer with a thermistor that monitors the temperature of the ceramic cover. Alternatively, the current supplied as an energy source to the light source can be monitored. In either case, the desired radiation level, sensed temperature or sensed current level can be correlated mathematically or empirically to a desired treatment regime for a given configuration of slide holders and treatment liquid type (e.g., aqueous treating liquid without IR absorbing stains might have different characteristics than organic treating liquids or aqueous stain solutions with IR absorbing chromophores).

Thus, if employing the wet chamber inductively heated as in U.S. Ser. No. 775,864, one can establish 60 minutes at a chamber temperature of 37° C. as suitable (for the primary antibody incubation step in the multistep method illustrated in U.S. Ser. No. 775,864), then the corresponding step in the present invention should be designed to quickly bring the treating fluid to or above 37° C. Infrared radiation offers advantages over convection heating even with the same treatment temperature because much of the 60 minutes in the prior method is actually spent warming the primary antibody solution up to 37° C. Infrared radiation can accomplish the warming to temperature in seconds or, at most, one or two minutes. Furthermore, the treatment temperature can usually be raised further, so as to further accelerate the step, provided that it is not raised so far as to cause deleterious effects (such as primary antibody or detection enzyme denaturation). As described below, a step such as primary antibody reaction with tissue has been found to be accomplished with infrared radiation in two minutes at a temperature of the antibody solution not precisely measured.

Additionally, since infrared radiation can be applied over a continuous range of intensities and can be programmed to be constant or variable in intensity over a treatment period, a variety of treatment temperature profiles can be established. Thus, for DNA hybridization steps, formalin fixed tissue samples containing double stranded DNA can be contacted with treating solution containing a labeled probe (e.g., labeled with biotin) and the assemblage subjected to infrared radiation to rapidly bring the liquid and adjacent sample to a denaturation temperature (90° to 105° C.). Depending upon the amount of cross-linking fixation used and the sensitivity of the tissue to overshooting the desired temperature, such heat-up can occur in as little as 5 minutes or less. If the radiation source is then lowered in intensity, the tissue sample and treating liquid will rapidly cool down to a hybridization temperature (e.g., 37° to 42° C.), which can be maintained by controlled continuous or periodic emission of infrared radiation. This hybridization temperature may be selected by adjusting the salt and formamide concentration in the hybridization mixture, based upon the well-known relationship between these concentrations and effective hybridization temperature. It is also suitable, but not necessary, to remove the slide assembly from the treatment chamber after the denaturation step and have the renaturation step occur in another chamber (which may or may not be equipped for infrared radiation) or elsewhere as the tissue samples and liquid cool down. Under such circumstances, as little as 1 to 5 minutes at the renaturation temperature may suffice for labeled probe (provide in excess in the treating fluid) to bind efficiently to the completely denatured DNA in the tissue sample.

Other such protocols of radiation intensity and/or temperature can be established empirically for various individual treatment steps (e.g., staining, binding, hybridization, digesting, enzymatic color developing or other steps of various processes which are accelerated by temperatures over ambient). In multistep methods such as immunocytochemistry, it is contemplated that at least one, but usually several, steps can be accelerated by the use of infrared radiation according to the present invention.

As indicated above, it is also contemplated to generate infrared radiation outside of a treatment chamber and then convey it into the chamber: with fiber optics, mirrors, lenses, waveguides or other such means. The small portion of a top, side or bottom wall of the chamber through which the radiation passes into the chamber would generally represent only a fraction of the interior surface of the chamber, and thus not a significant source of leakage of infrared radiation.

In other cases, the method of the present invention employs a treatment chamber into which the surfaces, samples and treating liquid are introduced manually. Thus, as illustrated by present FIG. 6, a conventional slide warmer chamber can be modified to build an infrared radiation device into the cover member.

In still other cases, the method of the present invention can apply to surfaces bearing sample and covered with a thin layer of treating fluid which are conveyed past a source of infrared radiation. Such embodiments can be illustrated with reference to U.S. Pat. Nos. 3,431,886 to McCormick and Johnson (1969) and 4,200,056 to Johnson (1980), which illustrate a staining device similar to those marketed by Miles Laboratories, Inc. as a HEMA-TEK 2 hematology stainer. In such device, slide bearing samples (typically blood smears) are held, first, in a generally vertical orientation by identical grooves in two screw driven drives, one at each corner of the slide. Each slide is then tilted forwardly nearly 90 degrees at one point along the screw drives by an increased separation of the grooves. The slides are then carried along across a platen having a planar metal upper surface by the coordinated action of the screw drives. The planar metal upper surface of the platen functions as a planar metal undersurface under the slides. The slides are carried in this horizontal position so that the tissue sample or blood smear faces the underlying planar metal surface. A treating liquid such as a stain is injected upwardly through an orifice in a platen, and is spread by surface tension between the closely spaced surfaces of the platen and the slide. Excess liquid is then wiped from the slide as it leaves the platen. When the slide reaches the next platen, the first treating liquid is displaced by a second treating liquid applied through a second hole in the planar metal undersurface of the next platen as the slide moves along by the coordinated action of the screws.

At the end of the staining process, in some instances, the slide is heated (by blowing warm air) for purposes of drying. According to forms of the present invention, after such a slide had been exposed to certain treating liquids (e.g., Wright-Giesma stain), the slide could be conveyed past a source of infrared radiation to quickly bring the sample and adhering liquid to an elevated temperature (e.g., 37° C.) where the penetration of stain into the sample would be accelerated. It is contemplated, for example, to convey the horizontally moving slides past an overhead infrared light source so as to warm the samples and treating fluid on the front of the slides by radiant energy directed through the back of the slides.

Other illustrative geometries for practicing forms of the method of the present invention include conveying slide pairs horizontally through an infrared treatment chamber, where each slide pair is exposed to infrared radiation. Thus, for example, a single row of slide pairs can be conveyed through a thin chamber provided with vertically-extending infrared radiation sources on one or both long walls to direct infrared radiation into the gap through one or both slides of each slide pair.

Figure 1:
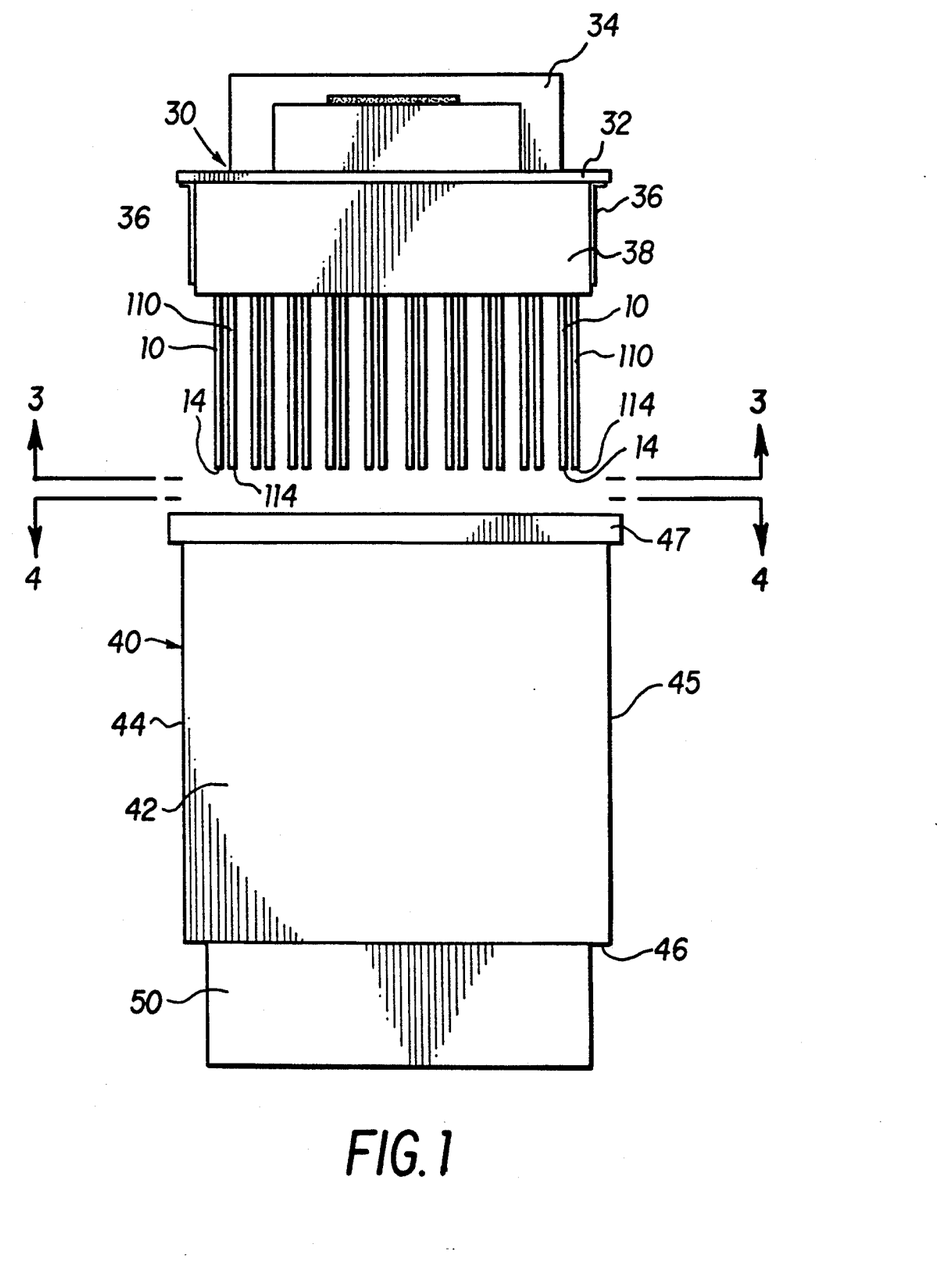
FIG. 1 is a front elevational view of a slide holder filled with slides above a treatment chamber according to a first embodiment of the present invention.

FIGS. 1–4 illustrate a first embodiment of the present invention. Referring first to FIG. 1, the slide holder 30 can be seen to include a horizontally extending cover 32, a top handle 34 on the cover 32, two angle brackets 36 extending downwardly from the cover 32 and a divider bracket 38 extending downwardly from the cover 32 between the angle brackets. The divider bracket 38 seen in this view is one of six such divider brackets 38 (described more fully below in connection with FIG. 3 and illustrated as divider brackets 147a–147f in U.S. Ser. No. 032,874). Extending downwardly from behind the bottom edge of the divider bracket 38 visible in this view are a plurality of slide pairs, ten of which are visible in this view. Each slide pair consists of a first slide 10 and a facing or second slide 110.

A treatment chamber 40 is shown in FIG. 1 below the bottom ends 14 and 114, respectively, of each first slide 10 and facing slide 110. In this view, the front wall 42, left wall 44, right wall 45 and bottom wall 46 of the generally rectangular treatment chamber 40 can be seen.

Figure 2:
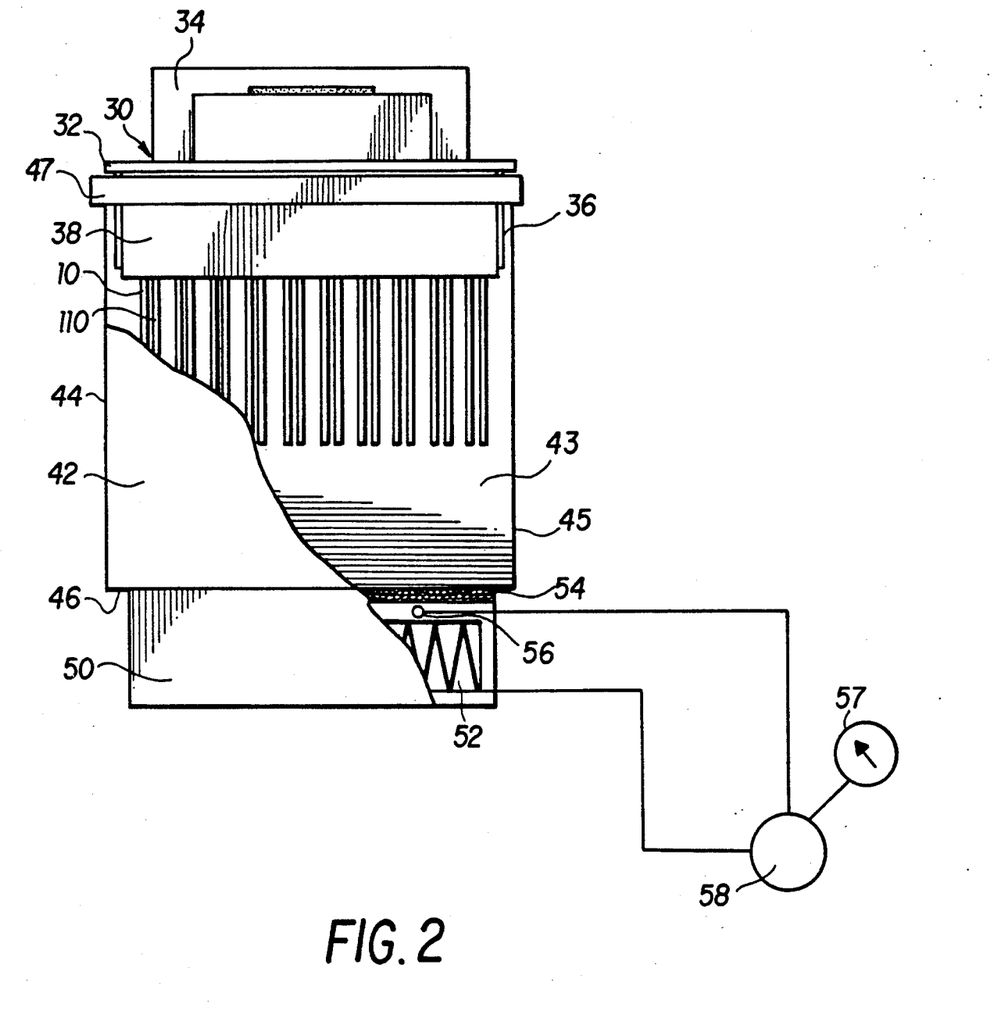
FIG. 2 is a front elevational view, partly in section, of the slide holder on the treatment chamber and the slides extending into the treatment chamber, all in accordance with the first embodiment.

The top handle 34 of the slide holder 30 can be lowered from the position shown in FIG. 1 (where the slides 10 and 110 are above and totally outside of the treatment chamber 40) to the position shown in FIG. 2 (where the slides 10 and 110 extend downwardly into the treatment chamber) either manually or by automated instruments. The preferred type of instrument for this purpose is based upon the HISTOMATIC slide stainer, model 172, available for a number of years from Fisher Scientific Company of Pittsburgh, Penna. (the present assignee). While such earlier versions of this instrument could be used; later versions, including one marketed since the middle of 1987 as the CODE-ON series of HISTOMATIC slide stainer (Fisher Catalog Number 15-185) are preferable because of enhanced control over the programming of the arm that engages handle 34. Included in that control is a solenoid that senses resistance as the handle 34 is lowered and then stops further downward movement. It is contemplated that treatment chamber 40 will be incorporated into such slide stainer, especially at the position designated Dryer 520 in FIG. 6 of U.S. Ser. No. 775,864 and of GB 2180647A, which position has previously been occupied by a slide drying station as described above.

Figure 4:
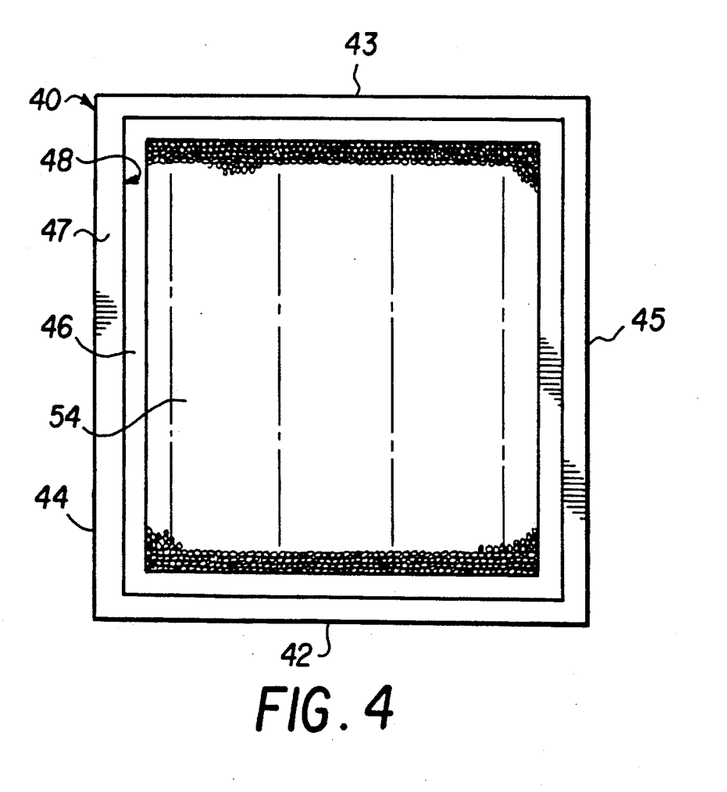
FIG. 4 is a top plan view, taken along line 4—4 in FIG. 1, showing the opening through the top of the treatment chamber.

Referring to FIGS. 2 and 4, the slide holder 30 covers the top of treatment chamber 40, with cover 32 extending horizontally over top opening 48 of treatment chamber 40. Angle brackets 36 rest on top wall portion 47, and it is this engagement which establishes a resistance to cause a conveyer arm to stop lowering slide holder 30.

The slides 10 and 110 extend downwardly from behind angle bracket 36 most, but not all of the distance downward to bottom wall 46 of treatment chamber 40. Upstanding left wall 44, right wall 45, back wall 43 and front wall 42 complete the enclosure of the slide array within treatment chamber 40. An infrared radiant heater device 50 sits on bottom wall 46 of treatment chamber 40 and includes a horizontally extending emitter element 52 (the light source) overlaid by a ceramic cover 54. In the illustrative commercially available radiant heater device 50 (from THERMA-TECH CORPORATION of South Paterson, N.J., and illustrated by the 4 inch by 6 inch (10×15 cm) type B infrared panel shown in their bulletin TT-0057-1-84 entitled, "THERMATECH INFRARED HEATERS AND SYSTEMS" and bearing a copyright date of 1983), the ceramic cover 54 is black and is transparent to far infrared radiation. Thus the light to which the bases of slides 10 and 110 is exposed is primarily in the 3.5 to 6.0 um portion of the far infrared. A thermocouple 56 is located under the ceramic cover 54. A thermistor or other similar device could also be used, and could be located under, on or above the ceramic cover 54. Alternatively, the themistor could be attached to the slides 10 or 110 (either on an exterior surface or on a surface between slide pairs underneath holder 30). A controller 58 is located outside the treatment chamber 40, to vary the current supplied to emitter element 52 based upon input from the thermocouple or thermistor 56 and external control information, illustrated by dial 57. Such control information is preferably provided by the control circuitry of a slide staining device (e.g., based upon a programmed value of X degrees Centigrade for Y seconds or minutes). As a result of the sensed temperature, the voltage supplied to emitter element 52 can be varied in a number of ways. In certain examples, the voltage continuously applied is varied. In a preferred embodiment, pulsed current is supplied, with the duration or frequency of the pulses being varied to control the rate of heat applied by the emitter element 52 over time to the slides.

Figure 3:
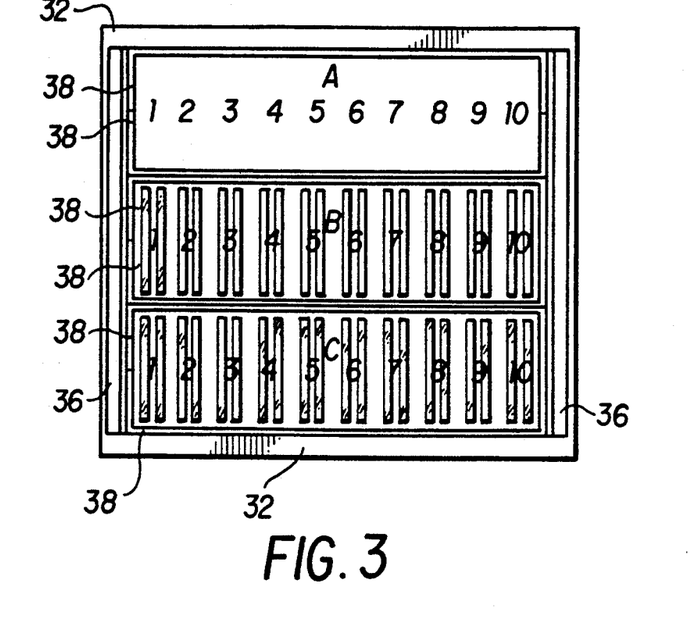
FIG. 3 is a bottom plan view, taken along line 3—3 in FIG. 1, showing the arrangement of slides in the slide holder.

FIG. 3 illustrates the arrangement of slides 10 and 110 in the slide holder 30 from a view taken along line 3—3 in FIG. 1 from beneath the bottom ends of the slides. This view is similar to FIG. 2B of U.S. Ser. No. 032,874; since, however that FIG. 2B shows the underside of a slide holder without slides inserted, it and the accompanying description in U.S. Ser. No. 032,874 can be consulted for further structural details of the slide holder designated 30 herein. Divider brackets 38 divide the underside of cover 32 into three rows (designated A, B and C by indicia on the underside of cover 32). As indicated in FIG. 2B of U.S. Ser. No. 032,874, further designations "1" through "10" can be provided on the underside of cover 32 to designate the ten slide pairs in one or each row. Lower clips (not shown) engage each side of each slide pair and press each slide 10 against the adjacent slide 110. Upper clips (not shown) similarly engage the slide pair above each lower clip. Coatings on one or both slides 10 and/or 110 (or shims) are present near the top end of each slide pair (see FIG. 2D of U.S. Ser. No. 032,874 for a better view of this) to maintain the gap of desired thickness (e.g., 150 um).

As can be seen in FIG. 3, cover 32 extends forwardly and rearwardly of the array of slides (forwardly and rearwardly of rows A, B and C). Angle brackets 36 also extend beyond the profile of rows A, B and C to the left and right. These outer portions of cover 32 and of brackets 36 can be thought of as a flange.

As can be seen in FIG. 4, the top plan view down into treatment chamber 40 shows the top wall portion 47 occupying only the perimeter of the horizontal profile of the treatment chamber 40. A top opening 48 occupies the central and major portion of the horizontal profile of treatment chamber 40.

Ceramic cover 54 can be seen on bottom wall 46, occupying somewhat less horizontal profile than top opening 48. Representative dimensions are 161 cm by 113 cm for the exterior of top wall portion 47, 148 cm by 95.5 cm for the overall treatment chamber below top wall portion 47, 97 cm by 92 cm for top opening 48 and 117 cm by 73.2 cm for ceramic cover 54.

Figure 5:
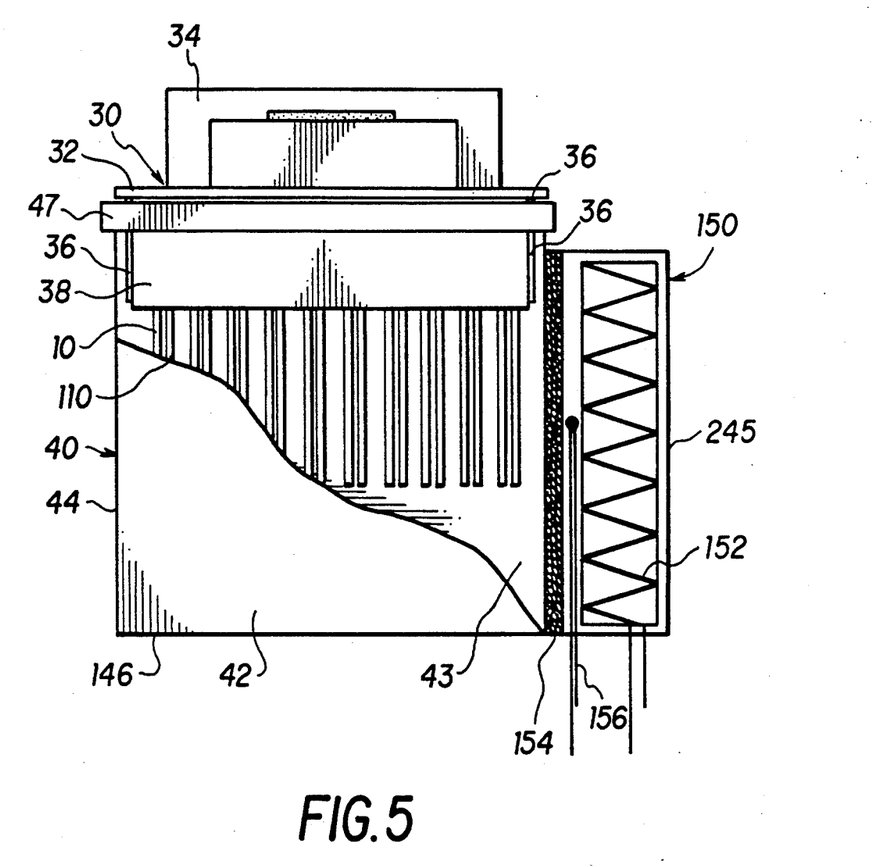
FIG. 5 is a front elevational view, partly in section, of a treatment chamber according to a second embodiment of the present invention.

FIG. 5 illustrates a modified treatment chamber 140. Elements 30, 32, 34, 36, 40, 42, 43, 44, and 47 in this view refer to elements identical to those bearing the same designations in FIGS. 1, 2 and 4. Radiant heating device 150 is located within an extension of a side wall 245 in this second embodiment rather than on the bottom wall as in the first embodiment. The bottom wall 146 shown in FIG. 5 is similar to bottom wall 46 in the prior figures, except that it is closed (rather than being occupied by ceramic element 54 as seen in FIG. 2). As described above, the interior of bottom wall 146 in FIG. 5 may be rendered reflective to infrared radiation so as to distribute radiation throughout chamber 40. The radiant heating device 150 consists of heating element 152, vertically extending ceramic cover 154 (where side wall 45 was in the earlier embodiments) and temperature probe 156, all within extended side wall 245. The sensing of temperature and operation of device 150 is similar to the operation of device 50 in the earlier embodiment.

It is also contemplated to modify the embodiment shown in FIG. 5 so as to tilt infrared radiation device 150 counterclockwise in the view of FIG. 5, so as to direct the radiation onto the reflective interior of bottom wall 46.

Figure 6:
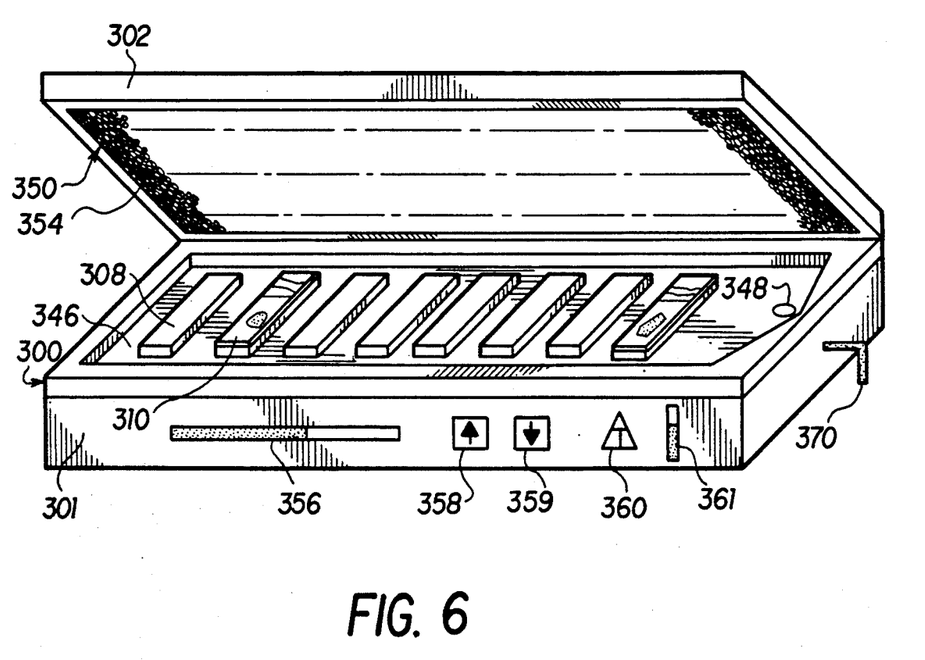
FIG. 6 is a perspective view of a treatment chamber for horizontally disposed slides, useful in a third embodiment of the method of the present invention.

As seen in FIG. 6, a slide warmer chamber 300 has a stationary base portion 301, to which is hingeably mounted a cover portion 302. As is conventional for slide warmers, a recessed portion 346 is formed in the top surface of base portion 301 and contains a series of parallel platforms 308 onto which slides 310 with specimens may be placed. The recessed portion 346, platforms 308 and cover portion 302 are dimensioned so that, when the cover portion 302 is closed, recessed portion 346 is a closed chamber with the tops of platforms 308 spaced sufficiently below cover portion 302 for air to circulate over slides 310 on some of platforms 308.

According to the present invention, an infrared radiation device 350 similar (except in dimensions) to devices 50 and 150, previously described, is built into the underside of cover portion 302. Accordingly, when cover portion 302 is closed, device 350 can be activated to expose slides 310 to infrared radiation.

Recessed portion 346 is also provided with a drain inlet 348 which connects to an external drain conduit 370 for removing liquid which flows off of slides 310 on platforms 308. This permits treating liquids to be applied (usually manually) and washed off. For those treating liquids that one wishes to accelerate, the cover portion 302 is closed and device 350 is activated, as described below. At the conclusion of a treating step, each such slide 310 can be rinsed, with the eluent flowing out through drain 348.

A variety of types of control for device 350 can be used. In FIG. 6, a gauge 356 for treatment level and a gauge 361 for treatment time are shown. Buttons 358, 359 and 360 are shown for, respectively, increasing, decreasing or changing the parameter to be set. Thus, before a particular treatment step, one could increase the treatment level shown on gauge 356 using button 358, then push button 360 and then increase the treatment time shown on gauge 351. If either parameter were to be lowered, button 359 would be used. Upon closing cover portion 302, device 350 would be brought to the treatment level shown on gauge 356 and held there for the treatment time shown on gauge 361. At the conclusion of that time period, device 350 would turn off and either cover 302 would automatically open or a signal would be sounded, or both.

Compared to the devices of FIGS. 1-5, the device of FIG. 6 is adapted for processing of smaller numbers of slides and for processes with fewer steps. The ways in which the temperature at the slide surface can be monitored, directly or indirectly, can be varied, with such monitor being built into the ceramic cover 354 on device 350 (as in the earlier embodiments), or built into platforms 308. The level set on gauge 361 can be either a power level applied to device 350 or a temperature level at platforms 308 that is maintained by regulating the voltage level or pulse duration supplied to device 350.

It is contemplated to modify the embodiment of FIG. 6 by covering each slide 310 first with liquid and then with a cover member whenever infrared radiation device 350 is to be used, especially for an extended period of time. The covering slide may cover all or a portion of slide 310 (but at least that portion bearing the sample) and may, in fact, create a slide pair with a capillary gap similar to slides 10 and 110 in earlier embodiments. In this way, the evaporation of liquid during radiation treatment can be retarded, and the liquid layer can be made more uniform so as to equalize temperature along the slide surface and between successive slides similarly exposed to infrared radiation.

In addition, if the cover slide is left on slide 310 throughout the subsequent processing and a capillary gap is formed below the cover slide and above slide 310, then subsequent liquids can be introduced into the gap by capillary action from the edge of the gap, and liquids can be withdrawn from the gap by blotting or exposing to vacuum the edge of the gap. U.S. Pat. Nos. 4,447,140 to Campbell et al (1984) discloses an example of how a cover member can form such gaps on a horizontally-extending slide, especially if multiple gaps are desired so as, for example, to cover multiple samples.

EXAMPLES

In each of the following Examples 1A-4B, a first portion (designated A) summarizes an existing treatment protocol used on one or more versions of the HISTOMATIC slide stainer by David J. Brigati, one of the applicants/designated inventors herein. Such description may or may not constitute prior art with respect to the present invention, but is provided primarily to illustrate applications for the present method and the times required for certain treating steps in the absence of infrared radiation. The succeeding portions of each such Example (designated B or C) illustrate how one or more steps of the multistep method described in A can be accelerated through the use of the present method.

EXAMPLE 1A

H&E HISTOLOGY STAINING

A standard procedure for staining histology specimens on the HISTOMATIC Slide Stainer, either the older Model 172 on the newer CODE-ON Series, is summarized in the following Table 1:

TABLE 1

| Event | Station | Time (min) | Mix? | Temp | Solution |
|---|---|---|---|---|---|
| 1 | 2 | 3.0 | Yes | Amb | Xylene |
| 2 | 3 | 2.0 | Yes | Amb | Xylene |
| 3 | 4 | 1.0 | Yes | Amb | 100% Ethanol |
| 4 | 5 | 0.5 | Yes | Amb | 95% Ethanol + Brij 35 |
| 5 | 0 | 0.5 | Yes | Amb | Water Bath |
| 6 | 6 | 2.0 | Yes | Amb | Hematoxylin |
| 7 | 0 | 1.0 | Yes | Amb | Water Bath |
| 8 | 12 | 0.2 | Yes | Amb | 0.1% Acid Alcohol |
| 9 | 0 | 1.0 | Yes | Amb | Water Bath |
| 10 | 11 | 0.5 | Yes | Amb | Ammonia Water |
| 11 | 0 | 0.5 | Yes | Amb | Water Bath |
| 12 | 10 | 0.5 | Yes | Amb | Eosin Y |
| 13 | 9 | 0.5 | Yes | Amb | 30% Ethanol |
| 14 | 8 | 0.5 | Yes | Amb | 95% Ethanol |
| 15 | 7 | 1.0 | Yes | Amb | 100% Ethanol |
| 16 | 1 | 2.0 | Yes | Amb | Xylene |

In the above Table I and all subsequent tables, "AMB" refers to ambient temperature (e.g., 20° C.) and a "YES" in the "MIX" column indicates that the rack of slides is moved by the instrument up and down (out of and into the solution) every 6 seconds during the indicated time at the indicated station. The times indicated do not include the short period in which the instrument conveys the slide array between stations.

In order to evaluate the effects of infrared radiation on certain steps of the process summarized in Table 1, a slide holder was placed in the HISTOMATIC Slide Stainer, CODE-ON Series. This holder, as illustrated in FIGS. 1, 2 and 3 hereof, had slots for thirty pairs of slides, each slide coated on the top 32 mm portion by a 75 um thick coating, and also coated at the bottom corners by a small triangular coating of similar thickness as shown in FIG. 2E of U.S. Ser. No. 032,874 and described more fully in U.S. Ser. No. 112,404 of Babbitt and Brigati, filed Oct. 26, 1987. Such slides are now commercially available from Fisher Scientific Company as PROBE-ON slides (Cat. No. 15-187M). In this particular experiment, 4 such slide pairs, with both slides of each pair bearing a thin section of paraffin embedded tissue, were placed in the holder. First, steps 1 and 2 of Table 1 were evaluated by contacting the bases of the slides (manually, outside the instrument) with xylene and then placing the array into a treatment chamber as shown in FIG. 2. A voltage regulator attached to the line current to emitter element 56 (see FIG. 52) was set at 50V, and the slides containing xylene were warmed for 20 seconds (carefully avoiding heating the xylene in each gap of a slide pair to above its flash point). Visually, the slides appeared totally dewaxed, but this result was further evaluated as follows. On the instrument, the slides were drained by placing their lower ends on a blotter and then introducing and blotting, successively: 100% alcohol, 100% alcohol, 100% alcohol, 95% alcohol, 95% alcohol, water with 0.25% of a 30% BRIJ 35 detergent solution in it and the hematoxylin solution of Station 6 (Harris's Hematoxylin) BRIJ 35 is Atlas Chemical's trademark for a nonionic detergent. After two minutes, the hematoxylin solution was out and the slides washed in tap water. The slides were microscope. The complete and uniform nuclear staining and penetration of the tissue by the hematoxylin indicated that paraffin was completely cleared in the presence of infrared radiation in only 20 seconds at one exposure, compared to a total of 5 minutes in two exposures in the prior method. When the same procedure was used, but the exposure of xylene-filled slides was 10 seconds instead of 20 seconds, the clearing was less complete, as evidenced by both visual and microscopic examination of the slides.

In similar fashion, 20 seconds in the infrared treatment chamber with the voltage regulator set at 50V was shown to suffice for step 16 of Table 1.

EXAMPLE 1C

The hematoxylin step of Table 1 (step 6) is usually accomplished in 2 minutes if the ambient temperature is 25° C., but more time is required if ambient temperature is lower (e.g., 6 minutes at 21° C.). When the treatment chamber and conditions described in Example 1B for this step were tried, complete staining of 5 um thick sections was demonstrated in 20 seconds.

EXAMPLE 2A

Employing the HISTOMATIC Slide Stainer as in Example 1A, a standard cytology procedure is as shown in Table 2:

TABLE 2

| Event | Station | Time (min) | Mix? | Temp | Solution |
|---|---|---|---|---|---|
| 1 | 5 | 3.0 | Yes | AMB | 95% Ethanol |
| 2 | 0 | 0.5 | Yes | AMB | Water Bath |
| 3 | 6 | 2.0 | Yes | AMB | Gill #1 Hematoxylin |
| 4 | 0 | 1.0 | Yes | AMB | Water Bath |
| 5 | 12 | 0.2 | Yes | AMB | 0.004% HCl |
| 6 | 0 | 0.5 | Yes | AMB | Water Bath |
| 7 | 11 | 1.0 | Yes | AMB | Scott's Tap Water |
| 8 | 0 | 0.5 | Yes | AMB | Water Bath |
| 9 | 10 | 2.0 | Yes | AMB | 95% Ethanol |
| 10 | 9 | 2.0 | Yes | AMB | Orange G6 |
| 11 | 10 | 0.5 | Yes | AMB | 95% Ethanol |
| 12 | 8 | 2.0 | Yes | AMB | Eosin Azure 65 |
| 13 | 7 | 1.0 | Yes | AMB | 100% Ethanol |
| 14 | 1 | 0.5 | Yes | AMB | 100% Ethanol |
| 15 | 2 | 0.2 | Yes | AMB | 100% Ethanol |
| 16 | 3 | 2.0 | Yes | AMB | Xylene |
| 17 | 4 | 1.0 | Yes | AMB | Xylene |

Such a process can be conducted on standard slides onto which a cellular smear has been applied and fixed in 50% alcohol. Directly transferring this process to slide pairs with capillary gaps, one would apply the smears to the PROBE-ON slide glass surfaces, apply 50% alcohol, air dry and appose the painted surfaces and insert into the slide holder.

EXAMPLE 2B

Employing two slide pairs in a holder as described in Example 1B, with human epithelial cheek cells smeared onto both slides of each of two slide pairs, the effects of infrared radiation on steps 1, 3, 10 and 12 of Table 2 were separately evaluated. In each case the voltage applied to the emitter element 52 was 100V, applied continuously. For step 1, 30 seconds in the treatment chamber sufficed to remove all of the carbowax fixative coating (sold by Clay-Adams division of Becton-Dickinson Corporation under their trademark SPRAY-CYTE) (see also page 1445 of Fisher Scientific Company's Fisher 88 Catalog) applied over the cellular smear. For step 10, 10 seconds in the treatment chamber sufficed to cause good staining with Orange G6. For steps 3 and 12, 20 seconds in the treatment chamber sufficed to cause good staining with Gill #1 hematoxylin (step 3) or with Eosin Azure (step 12).

EXAMPLE 3A

Table 3 illustrates a protocol for an immunocytochemistry staining procedure similar in concept that specified in U.S. Ser. No. 775,864 as exemplary. A number of specific differences, not particularly relevant to the present invention have been incorporated since the filing of that application by the common inventor

TABLE 3

| Event | Station | Time (min) | Temp | Solution |
|---|---|---|---|---|
| 1 | 6 | 3.0 | AMB | Xylene |
| 2 | 7 | 8.0 | 42 | Wet Chamber |
| 3 | 8 | 0.5 | | Blot |
| 4 | 6 | 0.1 | AMB | Xylene |
| 5 | 12 | 0.2 | | Blot |
| 6 | 6 | 0.1 | AMB | Xylene |
| 7 | 12 | 0.2 | | Blot |
| 8 | 6 | 0.1 | AMB | Xylene |
| 9 | 12 | 0.3 | | Blot |
| 10 | 5 | 0.1 | AMB | 100% Ethanol |
| 11 | 12 | 0.3 | | Blot |
| 12 | 5 | 0.1 | AMB | 100% Ethanol |
| 13 | 12 | 0.3 | | Blot |
| 14 | 4 | 0.1 | AMB | Methanol with 2% Hydrogen Peroxide |
| 15 | 12 | 0.3 | | Blot |
| 16 | 4 | 8.0 | AMB | Methanol with 2% Hydrogen Peroxide |
| 17 | 12 | 0.3 | | Blot |
| 18 | 3 | 0.1 | AMB | 95% Ethanol |
| 19 | 8 | 0.3 | | Blot |
| 20 | 3 | 0.1 | AMB | 95% Ethanol |
| 21 | 8 | 0.3 | | Blot |
| 22 | 3 | 0.1 | AMB | 95% Ethanol |
| 23 | 8 | 0.3 | | Blot |
| 24 | 10 | 0.1 | AMB | Buffer |
| 25 | 11 | 0.5 | | Blot |
| 26 | 10 | 0.1 | AMB | Buffer |
| 27 | 11 | 1.0 | | Blot |
| 28 | 14 | 0.5 | AMB | Protein Blocker |
| 29 | 9 | 1.0 | | Blot |
| 30 | 15 | 0.5 | AMB | Primary Antibody |
| 31 | 7 | 30.0 | 42 | Wet chamber |
| 32 | 9 | 1.0 | | Blot |
| 33 | 10 | 0.1 | AMB | Buffer |
| 34 | 9 | 0.3 | | Blot |
| 35 | 10 | 0.1 | AMB | Buffer |
| 36 | 11 | 0.3 | | Blot |
| 37 | 10 | 0.5 | AMB | Buffer |
| 38 | 11 | 1.0 | | Blot |
| 39 | 16 | 1.0 | AMB | Enz-labeled secondary antibody |
| 40 | 7 | 30.0 | 42 | Wet chamber |
| 41 | 9 | 1.0 | | Blot |
| 42 | 10 | 0.1 | AMB | Buffer |
| 43 | 9 | 0.5 | | Blot |
| 44 | 10 | 0.1 | AMB | Buffer |
| 45 | 9 | 0.5 | | Blot |
| 46 | | | | 35 Detergent |
| 47 | 9 | 1.0 | | Blot |
| 48 | 17 | 0.3 | AMB | Chromagen |
| 49 | 7 | 5.0 | 42 | Wet chamber |
| 50 | 9 | 1.0 | | Blot |
| 51 | 10 | 1.0 | AMB | Buffer |
| 52 | 9 | 0.5 | | Blot |
| 53 | 2 | 0.1 | AMB | Distilled water + Brij 35 Detergent |
| 54 | 9 | 1.0 | | Blot |
| 55 | 17 | 0.5 | AMB | Chromagen |
| 56 | 7 | 5.0 | 42 | Wet chamber |
| 57 | 9 | 1.0 | | Blot |
| 58 | 10 | 0.1 | AMB | Buffer |
| 59 | 9 | 0.5 | | Blot |
| 60 | 2 | 0.1 | AMB | Distilled water + Brij 35 Detergent |
| 61 | 9 | 0.5 | | Blot |
| 62 | 1 | 1.5 | AMB | Hematoxylin — water-based |
| 63 | 9 | 0.5 | | Blot |
| 64 | 2 | 0.1 | AMB | Distilled water + Brij 35 Detergent |
| 65 | 9 | 1.0 | | Blot |
| 66 | 2 | 0.3 | AMB | Distilled water + Brij 35 Detergent |
| 67 | 11 | 0.5 | | Blot |
| 68 | 10 | 0.6 | AMB | Buffer |
| 69 | 11 | 0.5 | | Blot |
| 70 | 2 | 0.1 | AMB | Distilled water + Brij 35 Detergent |
| 71 | 11 | 0.5 | | Blot |

The buffer in station 10, used in events 24, 26, 33, 35, 37, 42, 44, 51, 58 and 68, was a pH 7.5 Tris Biffe,. containing 0.1M Tris HCl, 0.1M NaCl and 0.25% of a 30% Brij 35 solution (obtained from Sigma Chemical). The distilled water with Brij 35 used in events 46, 60, 64, 66 and 70, contained 0.25% of such 30% Brij 35 solution. Such use of buffer and distilled water solutions with Brij 35 detergent is now preferred over the corresponding solution based upon Triton X100 described in U.S. Ser. No. 775,864. Particular attention should be drawn to events 31 and 40, which each consume 30 minutes of the overall process.

EXAMPLE 3B

A slide holder carrying four slide pairs, each slide bearing a formalin-fixed paraffin-embedded tissue section was carried by the HISTOMATIC Slide Stainer, CODE-ON Series instrument through the process of Table 3, except that a hold was placed in the program prior to the step of applying primary antibody (event 30). The holder was then removed from the instrument and the primary antibody was applied by manually contacting the bottom of the slide pairs with drops of the antibody solution placed in the correct wells of a reagent isolator. Examples of the antibodies used for this step include properly diluted rabbit anti-S100 protein at 1:100, rabbit anti-prostatic acid phosphatase at 1:100, guinea pig anti-insulin at 1:100 and mouse anti-carcinoembryonic antigen at 1:10. The slide holder was then placed in the treatment chamber shown in FIGS. 1, 2 and 4, in the position shown in FIG. 2, with the voltage applied to the emitter element 52 set at 50V, applied continuously for 1-2 minutes. In each experiment, the light source was initially at or near room temperature. The holder was then removed from the treatment chamber and placed back on the robotic arm of the instrument. The program was then resumed at event 32 of Table 3, through event 71. Microscopic examination of the slides revealed equivalent staining to similar sections stained in accordance with Example 3A.

EXAMPLE 3C

The same procedure as in Example 3B was followed, except that the hold was placed prior to event 39; the secondary antibody reagent (a mixture of goat anti-mouse and goat anti-rabbit antibodies conjugated to horseradish peroxidase) was then applied manually to the base of the slide pairs. Again, after 2 minutes in the treatment chamber with the voltage set at 50V continuously, the holder was returned to the instrument, which then resumed the process at event 41. Microscopic examination of the slides revealed equivalent staining to similar sections stained in accordance with Example 3A.

Although not tested to date, it should be possible to also accelerate other steps of the process of Table 3 by appropriate use of infrared radiation. In particular, based upon Example 2B, it should be apparent that step 2 of Table 1 (clearing with xylene) can be accelerated by infrared radiation. Other steps that might be so accelerated are chromogen development (events 49 and 56) and endogenous enzyme blocking (events 14 and 16).

EXAMPLE 4A

A suitable multi-step procedure for in situ DNA hybridization assays when performed on a modified version of the CODE-ON stainer is set forth in Table 4. With particular reference to step 50 a convection oven is present at station 19 (in place of the drying chamber) for the purpose of denaturing double-stranded DNA in the tissue section. A limited number of stainers so-modified have been sold by the present assignee, Fisher Scientific Company. This protocol, prior to the following modifications employing infrared radiation, represents collaborative work between Elizabeth R. Unger and David J. Brigati, Dr. Brigati being one of the present inventors.

TABLE 4

| Event | Station | Time (min) | Temp | Solution |
|---|---|---|---|---|
| 1 | 100 | 0.1 | | Oven On |
| 2 | 4 | 0.3 | | Xylene |
| 3 | 7 | 5.0 | 42 | Wet Chamber |
| 4 | 9 | 0.3 | | Blot |
| 5 | 4 | 0.3 | | Xylene |
| 6 | 7 | 5.0 | 42 | Wet Chamber |
| 7 | 9 | 0.3 | | Blot |
| 8 | 4 | 2.0 | | Xylene |
| 9 | 9 | 0.3 | | Blot |
| 10 | 4 | 1.5 | | Xylene |
| 11 | 9 | 0.3 | | Blot |
| 12 | 4 | 1.5 | | Xylene |
| 13 | 9 | 0.3 | | Blot |
| 14 | 4 | 1.5 | | Xylene |
| 15 | 9 | 0.3 | | Blot |
| 16 | 4 | 1.0 | | Xylene |
| 17 | 9 | 0.3 | | Blot |
| 18 | 5 | 1.0 | | 100% Ethanol |
| 19 | 9 | 0.3 | | Blot |
| 20 | 5 | 1.0 | | 100% Ethanol |
| 21 | 9 | 0.3 | | Blot |
| 22 | 5 | 1.0 | | 100% Ethanol |
| 23 | 9 | 1.0 | | Blot |
| 24 | 13 | 0.3 | | Enzyme (Pronase) |
| 25 | 7 | 10 | 42 | Wet Chamber |
| 26 | 9 | 0.3 | | Blot |
| 27 | 10 | 0.3 | | Buffer |
| 28 | 11 | 0.6 | | Blot |
| 29 | 10 | 1.0 | | Buffer |
| 30 | 11 | 0.6 | | Blot |
| 31 | 10 | 1.0 | | Buffer |
| 32 | 11 | 0.6 | | Blot |
| 33 | 10 | 1.0 | | Buffer |
| 34 | 11 | 0.6 | | Blot |
| 35 | 6 | 0.3 | | 95% Ethanol |
| 36 | 11 | 0.6 | | Blot |
| 37 | 6 | 0.3 | | 95% Ethanol |
| 38 | 11 | 0.6 | | Blot |
| 39 | 6 | 0.3 | | 95% Ethanol |
| 40 | 11 | 0.6 | | Blot |
| 41 | 5 | 0.3 | | 100% Ethanol |
| 42 | 11 | 0.6 | | Blot |
| 43 | 5 | 0.3 | | 100% Ethanol |

TABLE 4-continued

| Event | Station | Time (min) | Temp | Solution |
|---|---|---|---|---|
| 44 | 11 | 0.6 | | Blot |
| 45 | 5 | 0.3 | | 100% Ethanol |
| 46 | 11 | 0.6 | | Blot |
| 47 | 5 | 0.3 | | 100% Ethanol |
| 48 | 11 | 4.0 | | Blot |
| 49 | 14 | 2.0 | | Probe Reagent |
| 50 | 19 | 15 | 105 | Denaturing Oven |
| 51 | 0 | 3.0 | | Cool Down In Air To Near 42 C. |
| 52 | 7 | 60 | 42 | Wet Chamber for Hybridization |
| 53 | 9 | 1.0 | | Blot |
| 54 | 1 | 2.0 | | 2 × SSC Buffer |
| 55 | 9 | 0.6 | | Blot |
| 56 | 2 | 2.0 | | 0.2 × SSC Buffer |
| 57 | 11 | 0.6 | | Blot |
| 58 | 3 | 2.0 | | 0.16 × SSC Buffer |
| 59 | 11 | 0.6 | | Blot |
| 60 | 3 | 2.0 | | 0.16 × SSC Buffer |
| 61 | 11 | 0.6 | | Blot |
| 62 | 1 | 1.0 | | 2 × SSC Buffer |
| 63 | 11 | 0.6 | | Blot |
| 64 | 15 | 1.0 | | Albumin Blocker |
| 65 | 9 | 0.6 | | Blot |
| 66 | 15 | 2.0 | | Albumin Blocker |
| 67 | 11 | 2.0 | | Blot |
| 68 | 16 | 1.0 | | Detection System |
| 69 | 7 | 20 | 42 | Wet Chamber |
| 70 | 9 | 0.6 | | Blot |
| 71 | 10 | 2.0 | | Buffer |
| 72 | 9 | 0.6 | | Blot |
| 73 | 10 | 2.0 | | Buffer |
| 74 | 9 | 0.6 | | Blot |
| 75 | 10 | 2.0 | | Buffer |
| 76 | 11 | 0.6 | | Blot |
| 77 | 10 | 2.0 | | Buffer |
| 78 | 11 | 0.6 | | Blot |
| 79 | 17 | 0.5 | | Chromogen |
| 80 | 11 | 0.6 | | Blot |
| 81 | 17 | 1.0 | | Chromogen |
| 82 | 7 | 60 | 42 | Wet Chamber For Enzymatic Development Of Color |
| 83 | 9 | 0.6 | | Blot |
| 84 | 8 | 0.5 | | Distilled Water + Brij 35 |
| 85 | 9 | 0.6 | | Blot |
| 86 | 18 | 1.0 | | Hematoxylin (water-based) |
| 87 | 9 | 0.6 | | Blot |
| 88 | 8 | 1.0 | | Distilled Water + Brij 35 |
| 89 | 9 | 0.6 | | Blot |
| 90 | 8 | 1.0 | | Distilled Water + Brij 35 |
| 91 | 11 | 0.6 | | Blot |
| 92 | 10 | 1.0 | | Buffer |
| 93 | 11 | 0.6 | | Blot |

Detergent is provided in the following reagents: Station 10: The buffer contained 0.1 M Tris HCl, 0.1 M NaCl, pH 7.4 and 0.25% of a 30% Brij 35 solution. Station 8: Distilled water contains 0.25% of a 30% Brij 35 solution. In stations 1, 2 and 3, the 2×SSC, 0.2×SSC and 0.16×SSC buffers (SSC referring to standard sodium citrate buffers used in hybridization work) each contained 0.1% sodium dodecylsulfate.

The albumin blocker used in station 15 was a 1% solution of bovine serum albumin. Other reagents used were conventional.

Exemplary combinations of probe reagent (station 14), detection system (station 16) and chromogen (station 17) that can be used in this procedure are biotin labeled probe, avidin-alkaline phosphatase detection system and the binary chromogens BCIP+INT or BCIP+NBT. The same biotin labeled probes can be detected with avidin-horseradish peroxidase and the chromagen 3-amino, 9-ethylcarbazole. With minor modification to the procedure, other such combinations, such as dinitrophenyl-labeled probes with anti-DNP antibody HRP conjugate as detection system, HAIT-modified probe with anti-HAIT antibody HRP conjugate as detection system can be used. Sulfonated DNA probes can be used in this system with alkaline phosphatase-conjugated or horseradish peroxidase-conjugated anti-DNA sulfonate antibodies. One could also use a probe directly linked to an enzyme in station 14 and leaving station 16 empty.

Particular features of the process of Table 4 of interest to the present invention include steps 3, 6, 25 and 82, each of which should be accelerated by the use of infrared radiation by analogy to earlier examples, and events 50–52, which are in some sense unique for hybidization assays.

EXAMPLE 4B

A holder as described previously in Example 1B was filled with three slide pairs, each slide bearing a paraffin-embedded adrenal gland section 5 um thick known to contain herpes virus. The procedure was carried through event 49 as in Example 4A. At this point, instead of placing the holder into a denaturing oven set at 105° C. for 15–20 minutes, the holder was placed into the treatment chamber of present FIGS. 1, 2 and 4, with the slides projecting into the treatment chamber as shown in FIG. 2. Several different permutations were tried as to the starting condition of the light source 52 at the time the slides were introduced (cold, warm but off and on). In one such experiment, with the light source 52 being cold, 3 minutes at a voltage setting of 100V were employed. The holder was then returned to the instrument, and the process resumed at event 51 of Table 4. In this particular experiment, the probe was whole herpes virus genomic DNA labeled with biotin and the tissue substrates were paraffin-embedded section of an adrenal gland infected with a type 2 strain of the virus. Microscopic examination of the slides at the conclusion of the process showed staining equivalent to that achieved when the slides were subjected during step 50 to fifteen minutes in an oven preheated to 105° C.

It is also believed that the 60 minutes of step 52 (in the wet chamber) can be replaced by a much shorter time period in the treatment chamber equipped with infrared device. For example, it should be possible to merely shut off the voltage to the light source at the conclusion of the denaturing step and permit the fluid in the gaps to cool down to a desired rehybridization temperature (e.g., 37° C.). At such temperature, rehybridization should be substantially complete in five–ten minutes, depending on the type of probe and sample used.

What is claimed is:

1. A method for treating a thin sample on a surface which comprises:
   (a) providing a thin sample on a first surface,
   (b) maintaining a second surface substantially parallel to and spaced by a first distance from the first surface, thereby providing a gap between the first and second surfaces,
   (c) introducing a treating liquid into the gap,
   (d) drawing the treating liquid by capillary action within the gap into contact with the thin sample, and
   (e) generating infrared radiation so as to expose the treating liquid in contact with the thin sample to the infrared radiation for a sufficient exposure level and time to accelerate the treatment of the thin sample by the treating liquid.

2. The method of claim 1 wherein the introducing step (c) comprises contacting an edge of the gap with treating liquid.

3. The method of claim 2 wherein the first and second surfaces extend substantially vertically during the introducing step (c), drawing step (d) and generating step (e).

4. The method of claim 1 wherein a plurality of first surfaces are each provided with a thin sample, a second surface is maintained substantially parallel to and spaced by the first distance from each first surface; and treating liquid is introduced into each gap and is drawn by capillary action into contact with each thin sample; and wherein the treating liquid in contact with each thin sample is exposed to the infrared radiation.

5. The method of claim 1 wherein, after the drawing step (d), the first and second surfaces are conveyed into a treatment chamber, and wherein during the generating step (e) the infrared radiation is generated within the treatment chamber.

6. The method of claim 1 further comprising the step:
   (f) monitoring the temperature generated by the infrared radiation.

7. A method for accelerating the treatment of a biological specimen by a treating liquid which comprises the steps:
   (a) providing a thin sample on a portion of a first surface,
   (b) forming a thin layer of a treating liquid on the first surface in contact with the thin sample,
   (c) generating infrared radiation, and
   (d) exposing the thin layer of treating liquid to the infrared radiation at a sufficient exposure level and for a sufficient exposure time to accelerate the treatment of the thin sample by the treating liquid.

8. The method of claim 7 wherein the thin sample contains nucleic acid having a target nucleotide sequence and the treating liquid contains a nucleic acid probe having a target binding region substantially complementary to the target nucleotide sequence, and wherein the exposing step (d) the exposure level and exposure time are sufficient to accelerate the hybridization of the target binding region to the target nucleotide sequence.

9. The method of claim 8 wherein the nucleic acid in the thin sample is in double-stranded form, and wherein the exposing step (d) the exposure level and exposure time are sufficient to melt the double-stranded nucleic acid and for the target binding region to then hybridize to the target nucleotide sequence of a melted strand of the nucleic acid of the sample.

10. The method of claim 7 wherein the thin sample contains an antigenic site and wherein the treating liquid contains an antibody specific for the antigenic site and, wherein the exposing step (d), the exposure level and exposure time are sufficient to accelerate the binding of antibody to antigenic site.

11. The method of claim 7 wherein the treating liquid contains a stain.

12. The method of claim 7 further comprising the step:
   (e) monitoring the temperature generated by the infrared radiation.

13. The method of claim 12 wherein the monitoring step (e), a temperature adjacent to a source of infrared radiation is monitored.

14. The method of claim 12 wherein the monitoring step (e), a temperature adjacent to the thin layer of treating liquid is monitored.

15. A device for accelerated treatment of thin samples by treating liquid which comprises:
    (a) a treatment chamber having a bottom wall and upstanding side walls, the treatment chamber forming an upper opening,
    (b) holding means for engaging the upper ends of a plurality of planar pieces and maintaining the planar pieces in parallel array extending downward from the holding means in a substantially vertical direction,
    (c) flange means associated with the holding means for cooperating with the holding means to substantially cover the upper opening formed by the treatment chamber, and
    (d) radiation means for generating infrared radiation within the treatment chamber with the flange means and holding means substantially covering the upper opening and for exposing the planar pieces to the infrared radiation.

16. The device of claim 15 wherein the radiation means comprises a light source for infrared radiation within the treatment chamber.

17. The device of claim 16 wherein the radiation means extends horizontally and is adjacent to the bottom wall of the treatment chamber.

18. The device of claim 16 wherein the radiation source extends vertically and is adjacent to an upstanding side wall of the treatment chamber.

19. The device of claim 15 wherein the radiation means comprises a light source for infrared radiation located outside of the treatment chamber and a light conduit for conveying infrared radiation from the light source into the treatment chamber.

20. The device of claim 19 wherein the light conduit is a fiber optic.

21. The device of claim 15 further comprising:
    (e) monitoring means for monitoring the temperature generated by the infrared radiation.

22. The device of claim 21 wherein the monitoring means monitors a temperature adjacent to the radiation means.

23. The device of claim 21 wherein the monitoring means monitors a temperature adjacent to the planar pieces held by the holding means.

24. The device of claim 15 wherein the holding means maintains a plurality of pairs of pieces in parallel vertical orientation, with a first piece of each pair being spaced from the second piece of each pair by a first distance sufficiently small to maintain liquid in a gap between the first and second pieces by capillary action.

* * * * *